(12) United States Patent
de la Rama et al.

(10) Patent No.: US 11,559,658 B2
(45) Date of Patent: *Jan. 24, 2023

(54) FLEXIBLE TIP CATHETER WITH EXTENDED FLUID LUMEN

(71) Applicant: ST. JUDE MEDICAL, ATRIAL FIBRILLATION DIVISION, INC., St. Paul, MN (US)

(72) Inventors: Alan de la Rama, Cerritos, CA (US); Cary Hata, Irvine, CA (US); William Du, Walnut, CA (US); Yongxing Zhang, Irvine, CA (US)

(73) Assignee: St. Jude Medical, Atrial Fibrillation Division, Inc., St. Paul, MN (US)

( * ) Notice: Subject to any disclaimer, the term of this patent is extended or adjusted under 35 U.S.C. 154(b) by 517 days.

This patent is subject to a terminal disclaimer.

(21) Appl. No.: 16/742,428

(22) Filed: Jan. 14, 2020

(65) Prior Publication Data

US 2020/0206456 A1 Jul. 2, 2020

Related U.S. Application Data

(63) Continuation of application No. 15/639,981, filed on Jun. 30, 2017, now Pat. No. 10,576,244, which is a
(Continued)

(51) Int. Cl.
*A61B 18/14* (2006.01)
*A61M 25/00* (2006.01)
(Continued)

(52) U.S. Cl.
CPC ........ *A61M 25/007* (2013.01); *A61B 18/1492* (2013.01); *A61M 25/0074* (2013.01);
(Continued)

(58) Field of Classification Search
CPC .......... A61B 18/1492; A61B 2218/002; A61B 2018/1472; A61B 2018/00577;
(Continued)

(56) References Cited

U.S. PATENT DOCUMENTS 4,325,374 A  4/1982 Komiya
5,163,005 A  11/1992 Greene et al.
(Continued)

FOREIGN PATENT DOCUMENTS

EP  109178 A2  5/1984
JP  2002513652 A  5/2002
(Continued)

OTHER PUBLICATIONS

"International Search Report and Written Opinion of the International Searching Authority", PCT/US2010/049836 dated Nov. 15, 2010. 14 pages.
(Continued)

*Primary Examiner* — Thomas A Giuliani
(74) *Attorney, Agent, or Firm* — Armstrong Teasdale LLP

(57) ABSTRACT

A lumen extension member is provided for a catheter having a catheter body and an elongate electrode coupled to the catheter body. The elongate electrode defines an electrode lumen extending therethrough. The lumen extension member is positioned within the electrode lumen and is coupled to the catheter body. The lumen extension member includes a tubular member including a sidewall and at least one opening that extends through the sidewall.

19 Claims, 6 Drawing Sheets

Related U.S. Application Data continuation of application No. 14/613,294, filed on Feb. 3, 2015, now Pat. No. 9,724,492, which is a continuation of application No. 12/651,074, filed on Dec. 31, 2009, now Pat. No. 8,979,837, which is a continuation-in-part of application No. 11/853,759, filed on Sep. 11, 2007, now Pat. No. 8,187,267, said application No. 12/651,074 is a continuation-in-part of application No. 11/696,657, filed on Apr. 4, 2007, now Pat. No. 8,517,999.

(60) Provisional application No. 60/939,799, filed on May 23, 2007.

(51) Int. Cl.
  A61B 18/00 (2006.01)
  A61M 25/10 (2013.01)
  A61B 5/24 (2021.01)

(52) U.S. Cl.
  CPC ........ *A61B 5/24* (2021.01); *A61B 2018/00011* (2013.01); *A61B 2018/00101* (2013.01); *A61B 2018/00577* (2013.01); *A61B 2018/00821* (2013.01); *A61B 2018/00839* (2013.01); *A61B 2018/1465* (2013.01); *A61B 2218/002* (2013.01); *A61M 25/008* (2013.01); *A61M 25/0026* (2013.01); *A61M 25/0082* (2013.01); *A61M 2025/1047* (2013.01)

(58) Field of Classification Search
  CPC .......... A61B 2018/00011; A61B 2018/00029; A61B 2018/1465; A61B 2018/147; A61B 2018/00214; A61B 2018/0022; A61B 2018/00267; A61B 2018/00273; A61B 2018/00279; A61B 2018/00285; A61M 25/0074
  USPC ........... 606/41, 42, 47, 49, 40; 607/99, 101, 607/104, 105, 113, 115, 116
  See application file for complete search history.

(56) References Cited

U.S. PATENT DOCUMENTS

| | | |
|---|---|---|
| 5,163,905 A | 11/1992 | Don Michael |
| 5,279,299 A | 1/1994 | Imran |
| 5,364,352 A | 11/1994 | Cimino et al. |
| 5,378,230 A | 1/1995 | Mahurkar |
| 5,462,521 A | 10/1995 | Brucker et al. |
| 5,487,385 A | 1/1996 | Avitall |
| 5,520,682 A | 5/1996 | Baust et al. |
| 5,545,200 A | 8/1996 | West et al. |
| 5,569,220 A | 10/1996 | Webster, Jr. |
| 5,643,197 A | 7/1997 | Brucker et al. |
| 5,681,280 A | 10/1997 | Rusk et al. |
| 5,688,267 A | 11/1997 | Panescu et al. |
| 5,772,642 A | 6/1998 | Ciamacco et al. |
| 5,792,140 A | 8/1998 | Tu et al. |
| 5,800,428 A | 9/1998 | Nelson et al. |
| 5,810,802 A | 9/1998 | Panescu et al. |
| 5,833,632 A | 11/1998 | Jacobsen et al. |
| 5,853,425 A | 12/1998 | Houser |
| 5,893,885 A | 4/1999 | Webster, Jr. |
| 5,902,328 A * | 5/1999 | LaFontaine ........ A61B 18/1492 607/116 |
| 5,919,188 A | 7/1999 | Shearon et al. |
| 5,944,022 A | 8/1999 | Nardella et al. |
| 5,951,471 A | 9/1999 | De La Rama et al. |
| 5,954,719 A | 9/1999 | Chen et al. |
| 5,992,418 A | 11/1999 | De La Rama et al. |
| 6,001,005 A | 12/1999 | Anderson, III et al. |
| 6,001,095 A | 12/1999 | De La Rama et al. |
| 6,003,080 A | 12/1999 | Ratcliff et al. |
| 6,010,500 A | 1/2000 | Sherman et al. |
| 6,017,338 A | 1/2000 | Brucker et al. |
| 6,030,382 A | 2/2000 | Fleischman et al. |
| 6,053,912 A | 4/2000 | Panescu et al. |
| 6,063,080 A | 5/2000 | Nelson et al. |
| 6,080,151 A | 6/2000 | Swartz et al. |
| 6,171,275 B1 | 1/2001 | Webster |
| 6,210,400 B1 | 4/2001 | Hebert et al. |
| 6,210,409 B1 | 4/2001 | Ellman et al. |
| 6,217,573 B1 | 4/2001 | Webster |
| 6,233,476 B1 | 5/2001 | Strommer et al. |
| 6,235,022 B1 | 5/2001 | Hallock et al. |
| 6,251,134 B1 | 6/2001 | Alt et al. |
| 6,273,876 B1 | 8/2001 | Klima et al. |
| 6,308,090 B1 | 10/2001 | Tu et al. |
| 6,325,797 B1 | 12/2001 | Stewart et al. |
| 6,346,104 B2 | 2/2002 | Daly et al. |
| 6,356,790 B1 | 3/2002 | Maguire et al. |
| 6,379,349 B1 | 4/2002 | Muller et al. |
| 6,385,472 B1 | 5/2002 | Hall et al. |
| 6,405,067 B1 | 6/2002 | Mest et al. |
| 6,464,632 B1 | 10/2002 | Taylor |
| 6,493,590 B1 | 12/2002 | Wessman et al. |
| 6,498,944 B1 | 12/2002 | Ben Haim et al. |
| 6,522,930 B1 * | 2/2003 | Schaer ............... A61B 18/1492 607/104 |
| 6,604,003 B2 | 8/2003 | Fredricks et al. |
| 6,611,699 B2 | 8/2003 | Messing |
| 6,662,034 B2 | 12/2003 | Segner et al. |
| 6,690,963 B2 | 2/2004 | Ben Haim et al. |
| 6,780,183 B2 | 8/2004 | Jimenez et al. |
| 6,788,967 B2 | 9/2004 | Ben Haim et al. |
| 6,796,966 B2 | 9/2004 | Thomas |
| 6,921,397 B2 | 7/2005 | Corcoran et al. |
| 6,980,843 B2 | 12/2005 | Eng et al. |
| 7,013,169 B2 | 3/2006 | Bowe |
| 7,137,395 B2 | 11/2006 | Fried et al. |
| 7,197,354 B2 | 3/2007 | Sobe |
| 7,263,397 B2 | 8/2007 | Hauck et al. |
| 7,386,339 B2 | 6/2008 | Strommer et al. |
| 7,389,148 B1 | 6/2008 | Morgan |
| 7,416,552 B2 | 8/2008 | Paul et al. |
| 7,468,027 B2 | 12/2008 | Barbut et al. |
| 7,536,218 B2 | 5/2009 | Govari et al. |
| 7,537,595 B2 | 5/2009 | McClurken |
| 7,537,596 B2 | 5/2009 | Jensen |
| 7,565,208 B2 | 7/2009 | Harris et al. |
| 7,615,050 B2 | 11/2009 | Cross et al. |
| 7,669,309 B2 | 3/2010 | Johnson et al. |
| 7,699,771 B2 | 4/2010 | Wendlandt |
| 7,706,891 B2 | 4/2010 | Hastings et al. |
| 7,815,635 B2 | 10/2010 | Wittkampf et al. |
| 7,824,406 B2 | 11/2010 | Wang et al. |
| 7,824,517 B2 | 11/2010 | Kampa et al. |
| 7,826,881 B1 | 11/2010 | Beatty et al. |
| 7,857,810 B2 | 12/2010 | Wang et al. |
| 7,873,401 B2 | 1/2011 | Shachar |
| 8,048,072 B2 | 11/2011 | Verin et al. |
| 8,187,267 B2 | 5/2012 | Pappone et al. |
| 8,979,837 B2 * | 3/2015 | de la Rama ........ A61M 25/007 606/41 |
| 9,289,257 B2 * | 3/2016 | Toth ................... A61B 5/1076 |
| 9,724,492 B2 * | 8/2017 | de la Rama ...... A61M 25/0074 |
| 10,576,244 B2 * | 3/2020 | de la Rama ........ A61M 25/007 |
| 2001/0012956 A1 | 8/2001 | Behl et al. |
| 2002/0058866 A1 | 5/2002 | Segner et al. |
| 2002/0072710 A1 | 6/2002 | Stewart et al. |
| 2002/0103426 A1 | 8/2002 | Segner et al. |
| 2002/0156420 A1 | 10/2002 | Anderson et al. |
| 2003/0088244 A1 | 5/2003 | Swanson et al. |
| 2003/0125730 A1 | 7/2003 | Berube et al. |
| 2004/0015215 A1 | 1/2004 | Fredricks et al. |
| 2004/0027106 A1 | 2/2004 | Martins |
| 2004/0034348 A1 | 2/2004 | Rashidi |
| 2004/0064158 A1 | 4/2004 | Klein et al. |
| 2004/0143256 A1 | 7/2004 | Bednarek |
| 2004/0153056 A1 | 8/2004 | Muller et al. |
| 2004/0181138 A1 | 9/2004 | Hindricks et al. |
| 2004/0204671 A1 | 10/2004 | Stubbs et al. |

(56) References Cited

U.S. PATENT DOCUMENTS

| | | |
|---|---|---|
| 2004/0220461 A1 | 11/2004 | Schwartz |
| 2004/0231683 A1 | 11/2004 | Eng et al. |
| 2004/0236350 A1 | 11/2004 | Lewis et al. |
| 2004/0243143 A1 | 12/2004 | Corcoran et al. |
| 2004/0267106 A1 | 12/2004 | Segner et al. |
| 2005/0004563 A1 | 1/2005 | Racz et al. |
| 2005/0043713 A1 | 2/2005 | Zhou |
| 2005/0049583 A1 | 3/2005 | Swanson |
| 2005/0054989 A1 | 3/2005 | McGuckin et al. |
| 2005/0070894 A1* | 3/2005 | McClurken ........ A61B 18/1492 606/50 |
| 2005/0096647 A1 | 5/2005 | Steinke et al. |
| 2005/0143729 A1 | 6/2005 | Francischelli et al. |
| 2005/0187561 A1 | 8/2005 | Lee Sepsick et al. |
| 2005/0197633 A1 | 9/2005 | Schwartz et al. |
| 2005/0204671 A1 | 9/2005 | Heuvel et al. |
| 2005/0272975 A1 | 12/2005 | McWeeney et al. |
| 2006/0004353 A1 | 1/2006 | Koyfman et al. |
| 2006/0009740 A1 | 1/2006 | Higgins et al. |
| 2006/0015126 A1 | 1/2006 | Sher |
| 2006/0064123 A1 | 3/2006 | Bonnette et al. |
| 2006/0149192 A1 | 7/2006 | Deniega et al. |
| 2006/0200191 A1 | 9/2006 | Zadno Azizi |
| 2006/0265043 A1 | 11/2006 | Mandrusov et al. |
| 2006/0278246 A1 | 12/2006 | Eng et al. |
| 2006/0287650 A1 | 12/2006 | Cao et al. |
| 2007/0005053 A1 | 1/2007 | Dando |
| 2007/0021743 A1 | 1/2007 | Rioux et al. |
| 2007/0060847 A1 | 3/2007 | Leo et al. |
| 2007/0073288 A1 | 3/2007 | Hall et al. |
| 2007/0156114 A1 | 7/2007 | Worley et al. |
| 2007/0179491 A1 | 8/2007 | Kratoska et al. |
| 2007/0270791 A1 | 11/2007 | Wang et al. |
| 2007/0299424 A1 | 12/2007 | Cumming et al. |
| 2008/0045943 A1* | 2/2008 | Wittkampf ......... A61B 18/1492 606/41 |
| 2008/0091193 A1 | 4/2008 | Kauphusman et al. |
| 2008/0091195 A1 | 4/2008 | Sliwa et al. |
| 2008/0139999 A1 | 6/2008 | Gibson et al. |
| 2008/0161788 A1 | 7/2008 | Dando et al. |
| 2008/0161789 A1 | 7/2008 | Thao et al. |
| 2008/0249522 A1 | 10/2008 | Pappone et al. |
| 2008/0275428 A1 | 11/2008 | Tegg et al. |
| 2008/0281319 A1 | 11/2008 | Paul et al. |
| 2008/0294158 A1 | 11/2008 | Pappone et al. |
| 2008/0300589 A1 | 12/2008 | Paul et al. |
| 2008/0312713 A1 | 12/2008 | Wilfley et al. |
| 2009/0012517 A1 | 1/2009 | De La Rama et al. |
| 2009/0018497 A1 | 1/2009 | Birchard et al. |
| 2009/0228092 A1 | 9/2009 | Raeder-Devens et al. |
| 2009/0247993 A1 | 10/2009 | Kirschenman et al. |
| 2009/0287210 A1 | 11/2009 | Kauphusman et al. |
| 2010/0004632 A1 | 1/2010 | Wu et al. |
| 2010/0152731 A1 | 6/2010 | De La Rama et al. |
| 2010/0174177 A1 | 7/2010 | Wu |
| 2011/0118582 A1 | 5/2011 | De La Rama et al. |
| 2012/0255130 A1 | 10/2012 | Bazito et al. |
| 2012/0265130 A1 | 10/2012 | De La Rama et al. |
| 2013/0085479 A1 | 4/2013 | De La Rama et al. |

FOREIGN PATENT DOCUMENTS

| | | |
|---|---|---|
| JP | 2006509547 A | 3/2006 |
| JP | 2007509693 A | 4/2007 |
| JP | 2008136875 A | 6/2008 |
| JP | 2008541799 A | 11/2008 |
| JP | 3162588 U | 9/2010 |
| JP | 2010533564 A | 10/2010 |
| WO | 9634652 A1 | 11/1996 |
| WO | 1996034652 A1 | 11/1996 |
| WO | 1999056812 A2 | 11/1999 |
| WO | 03049631 A1 | 6/2003 |
| WO | 2003049631 A1 | 6/2003 |
| WO | 2005048858 A1 | 6/2005 |
| WO | 2005094661 A1 | 10/2005 |
| WO | 2007015139 A2 | 2/2007 |
| WO | 2007035554 A1 | 3/2007 |
| WO | 2008010039 A2 | 1/2008 |
| WO | 2008124619 A1 | 10/2008 |
| WO | 2008147599 A1 | 12/2008 |
| WO | 2009120982 A2 | 10/2009 |
| WO | 2010129661 A1 | 11/2010 |
| WO | 2011159861 A2 | 12/2011 |

OTHER PUBLICATIONS

H. Krum et al., "Catheter-based renal sympathetic denervation for resistant hypertension: a multicentre safety and proof-of-principle cohort study", www.lhelancel.com, Mar. 30, 2009, pp. 1-7.

PCT International Search Report (PCT/US2008/069248), dated Jan. 15, 2009, 2 pages.

* cited by examiner

FLEXIBLE TIP CATHETER WITH EXTENDED FLUID LUMEN

CROSS REFERENCE TO RELATED APPLICATIONS

This patent application is a Continuation of U.S. patent application Ser. No. 15/639,981 filed Jun. 30, 2017, issued as U.S. Pat. No. 10,576,244, which is a Continuation of U.S. patent application Ser. No. 14/613,294 filed Feb. 3, 2015, issued as U.S. Pat. No. 9,724,492, which is a Continuation of U.S. patent application Ser. No. 12/651,074 filed Dec. 31, 2009, issued as U.S. Pat. No. 8,979,837, which is a Continuation-In-Part of U.S. patent application Ser. No. 11/696,657 filed Apr. 4, 2007, issued as U.S. Pat. No. 8,517,999, and a Continuation-In-Part of U.S. patent application Ser. No. 11/853,759 filed Sep. 11, 2007, issued as U.S. Pat. No. 8,187,267, which claims benefit of U.S. Provisional Application No. 60/939,799 filed May 23, 2007, the contents of which are hereby incorporated by reference in their entireties.

BACKGROUND

The subject matter disclosed herein generally relates to catheter devices and, more specifically, to an ablation catheter including an extended fluid lumen.

Catheters are flexible, tubular devices that are widely used by physicians performing medical procedures to gain access into interior regions of the body. Catheters with one or more electrodes are generally known in the surgical art. For example, electrode catheters can be and/or are used for electrically mapping a body part and/or delivering therapy to a body part.

Known ablation catheters include a main catheter body having a distal end and an ablation electrode coupled to the distal end of the main catheter body. Some known ablation catheters include an irrigation system to provide irrigation fluid to cool the ablation electrode. In at least some known catheter configurations, the irrigation fluid does not cool the ablation electrode substantially uniformly, and the irrigation fluid does not completely surround the ablation electrode.

Furthermore, known irrigated ablation catheters do not provide more irrigation fluid to the part of the ablation electrode that is in contact with the tissue material being ablated, and less irrigation fluid to the part of the ablation electrode that is not in contact with the tissue material.

BRIEF DESCRIPTION

Advantageous embodiments of catheters including electrodes are disclosed that provide, among other things, a radially directed irrigation flow that is substantially uniform along a longitudinal length of the electrode.

In one aspect, a lumen extension member is provided for a catheter having a catheter body and an elongate electrode. The lumen extension member includes a tubular member coupled to the catheter body and positioned within the elongate electrode. The tubular member includes a sidewall and at least one opening that extends through the sidewall.

In another aspect, a catheter including a body having a distal portion is provided. The catheter includes a tip assembly and a lumen extension member. The tip assembly defines a tip lumen extending therethrough and is coupled to the distal portion of the catheter body. The lumen extension member is positioned in the tip lumen and is coupled to the distal portion of the catheter body.

In yet another aspect, an ablation catheter is provided. The ablation catheter includes a catheter body having a distal portion and an elongate electrode that is coupled to the catheter body distal portion. The elongate electrode defines an electrode lumen extending therethrough. A lumen extension member is positioned in the electrode lumen and is coupled to the distal portion of the catheter body.

In some forms of the inventive irrigated catheter devices, the elongate electrodes can be and/or are formed of relatively inflexible material and are fabricated to provide flexibility and directionality of fluid egress therefrom when impinging upon a surface at an acute angle. For example, the electrode can be formed of a relatively thin metal cup that is laser cut into dovetail joints that become wide, or more open, toward the surface and tend to become closer, or less open, away from the surface. When such a flexible elongated electrode of an inventive irrigated catheter is impinged upon a surface, the flow of the irrigating fluid varies along the longitudinal length of the elongate electrode due to the variations in size of the openings or gaps formed by the joints when the electrode is in the flexed position. For example, more fluid flows toward the surface than away from the surface due to the joints becoming more open toward the surface and less open away from the surface.

BRIEF DESCRIPTION OF THE DRAWINGS

FIG. 5 is a cross-sectional view of the tip assembly shown in

FIG. 3;

FIG. 6 is a cross-sectional view of the tip assembly shown in

FIG. 4;

FIG. 9 is a top view of the lumen extension member shown in

FIG. 7;

DETAILED DESCRIPTION

Embodiments of ablation catheters including a tip assembly and an extended lumen are described. The extended lumen facilitates providing a radially directed irrigation pattern that is substantially uniform along a longitudinal length of the tip assembly when the tip assembly is in the unflexed, or relaxed state. In addition, the extended lumen provides a varying fluid flow along the longitudinal length of the elongate electrode due to the variations in size of the openings or gaps formed by the joints when the electrode is in the flexed position. For example, more fluid flows toward the surface than away from the surface due to the joints becoming more open toward the surface and less open away from the surface.

As described in more detail below, a catheter is provided that includes a tip assembly and a lumen extension member defining an extended lumen therethrough. The lumen extension member is positioned within the tip assembly and includes a sidewall having a plurality of openings extending therethrough. The plurality of openings may have a variety of different sizes, shapes, and orientations, enabling the catheter to channel a substantially uniform fluid flow along a longitudinal length of the tip assembly. The lumen extension member may have various configurations as explained below in numerous exemplary embodiments for both relatively traditional inflexible as well as novel flexible elongate electrodes.

Figure 1:
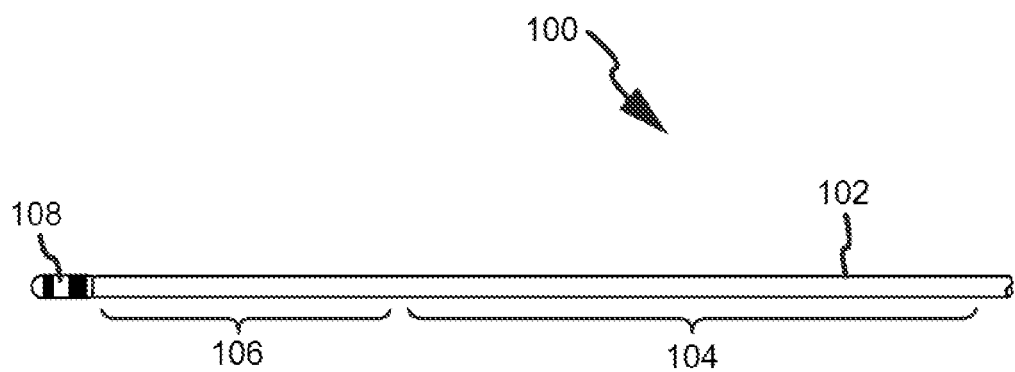
FIG. 1 is a perspective view of an exemplary catheter.

FIG. 1 is a perspective view of an exemplary catheter 100 including a flexible outer tube or tubing 102. Although it will become evident that aspects of exemplary catheter 100 are applicable to a variety of medical procedures and end uses, the exemplary embodiments will be described principally in the context of a specific example of an ablation catheter. However, the subject matter disclosed herein is not intended to be limited to any specific example.

Tubing 102 may include any suitable number of portions. In the exemplary embodiment, tubing 102 includes a proximal portion 104 and a distal portion 106. In the exemplary embodiment, a tip assembly 108 is coupled to tubing 102 and, more specifically, to a distal end of distal portion 106. Tubing 102 can have variable or consistent stiffness and can be pre-curved or deflectable as is known in the art.

Tubing 102 is fabricated using any suitable process, such as an extrusion process, from any suitable tubing material, such as engineered nylon resins and plastics, including but not limited to PEBAX® tubing of Ato Fina Chemicals, France. In the exemplary embodiment, proximal portion 104 is fabricated from a first tubing material, and distal portion 106 is fabricated from a second tubing material that is different from the first tubing material. The tubing material may include different materials and/or grades of materials for enhanced performance of tubing 102 in use of catheter 100.

Tubing 102, by virtue of portions 104 and 106 having varying flexible properties, is sometimes referred to as a multi-flexible tube. In the exemplary embodiment, the first material is a comparatively rigid and kink resistant braided material. More specifically, in the exemplary embodiment, proximal portion 104 is formed with different portions of braided material, semi-soft material, and soft material fused to one another so that proximal portion 104 becomes increasingly flexible along a longitudinal length of tubing 102. Moreover, the second material defining distal portion 106 is formed with a soft and flexible material having flexible properties. In the exemplary embodiment, portions 104 and 106 share a common outside diameter of, for example, 7 French, although in other embodiments, portions 104 and 106 have varied diameters.

In the exemplary embodiment, proximal portion 104 extends for a majority of the longitudinal length of tubing 102, and distal portion 106 extends for a length shorter than the length of proximal portion 104. More specifically, in the exemplary embodiment, proximal portion 104 extends for a longitudinal length of approximately 126.3 cm, and distal portion 106 extends for a longitudinal length of approximately 0.8 cm, although other relative lengths of tube portions 104 and 106 may likewise be employed in other embodiments. The different relative lengths of portions 104 and 106, as well as the different flexible properties of portions 104 and 106, enable tip assembly 108 to be more precisely positioned within a patient's body, while also avoiding problems of kinks and excessive deflection of tubing 102 along the majority of its length during use and handling.

During operation, distal portion 106 of catheter 100 including tip assembly 108 is navigated to a site in the body where a medical procedure, such as an atrial mapping, pacing and/or ablation, is to occur. Distal portion 106 may extend, for example, into a heart chamber of a patient.

Figure 2:
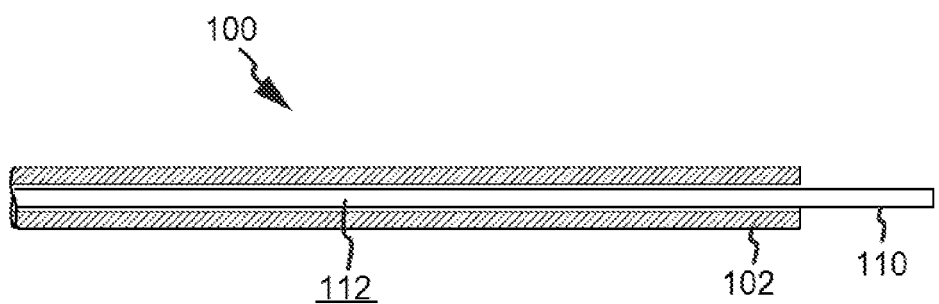
FIG. 2 is a cross-sectional view of the catheter shown in FIG. 1.

FIG. 2 is a cross-sectional view of catheter 100. In the exemplary embodiment, catheter 100 includes an inner tube 110 that defines a central lumen 112 extending therethrough. It should be understood that more than one inner tube 110, or lumen, can be implemented in a concentric or coaxial configuration or offset from the central axis of catheter 100. In the exemplary embodiment, inner tube 110 has an outer diameter that is smaller than an inner diameter of tubing 102 such that a space extends between an outer surface of inner tube 110 and an inner surface of tubing 102. Inner tube 110 can be and, in one embodiment, is a braided polyimide tube that maintains a flow path through central lumen 112 in all orientations of tip assembly 108 without compromising the flexibility of tubing 102.

Figure 3:
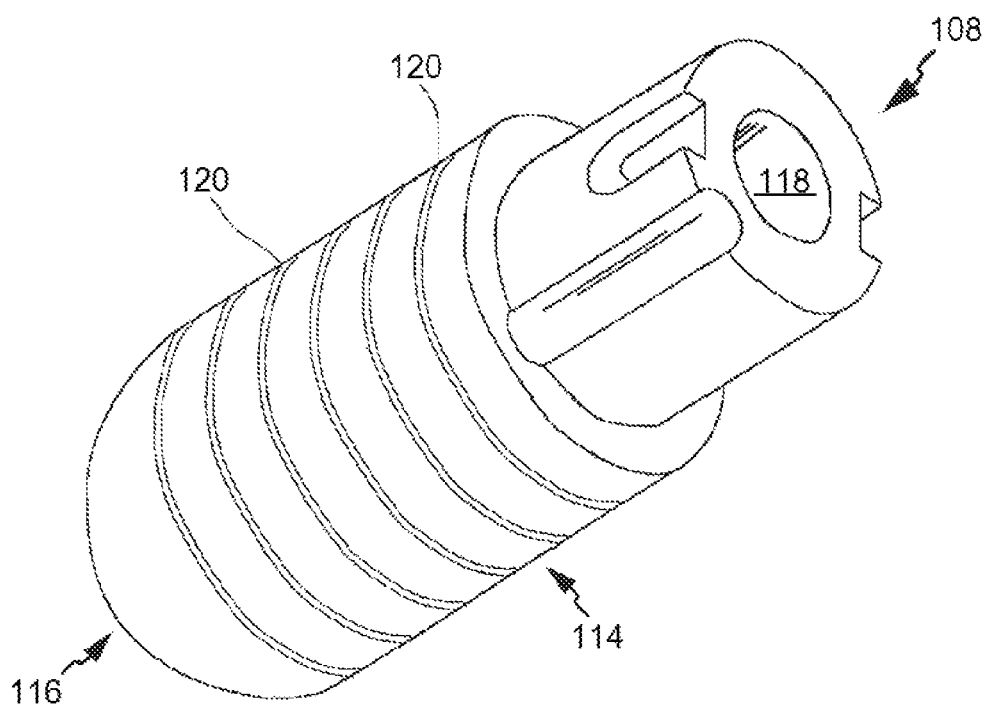
FIG. 3 is a perspective view of an exemplary tip assembly for use with the catheter shown in FIG. 1.

FIG. 3 is a perspective view of tip assembly 108. In the exemplary embodiment, tip assembly 108 is a flexible tip electrode including a generally cylindrical sidewall 114 and a dome tip 116. In the exemplary embodiment, tip assembly 108 defines a tip lumen 118 extending therethrough.

In the exemplary embodiment, sidewall 114 includes a plurality of annular surface channels 120 cut or otherwise formed into sidewall 114. In the exemplary embodiment, channels 120 define elongate areas of decreased wall thickness and decreased cross-sectional area of sidewall 114. In the exemplary embodiment, channels are configured to channel an irrigation fluid from an interior of tip assembly 108 to an exterior of tip assembly 108. In the exemplary embodiment, elongate channels 120 are structurally opened in a relaxed state and capable of opening more or less depending on the characteristics of a force vector imparted to tip assembly 108. In the exemplary embodiment, the areas of sidewall 114 that are not occupied by elongate channels 120 do not deform like the areas of sidewall 114 that are occupied by elongate channels 120. More specifically, in the exemplary embodiment, the areas of sidewall 114 that are occupied by elongate channels 120 are more flexible that the areas of sidewall 114 that are not occupied by elongate channels 120 and the elongate electrode sidewall is thus configured to flex and have variations in an opening size of said channels.

Channels 120 may have any suitable size and/or shape. In the exemplary embodiment, elongate channel 120 has a length that is at least about 3 times a width of channel 120 although it can be at least about 5 times or for that matter at least about 10 times or more. Moreover, in the exemplary embodiment, elongate channels 120 are oriented about tip assembly 108 and extend generally parallel to one another. At least one annular channel 120 extends in a plane that is generally perpendicular to a longitudinal length of tip assembly 108. Respective channels 120 can be and, in one embodiment, are spaced equidistant from each other along a longitudinal length of tip assembly 108. At least one annular channel 120 may form a continuous 360 degree unending loop that is circular.

In one embodiment, tip assembly 108 includes a membrane (not shown) extending across at least a portion of tip assembly 108 to facilitate separating an object (not shown) from channel 120. More specifically, in this embodiment, the membrane extends across an area of sidewall 114 that is occupied by channel 120 to facilitate inhibiting a tissue from being pinched within channel 120 when tip assembly 108 is flexed and/or bent. In this embodiment, the membrane is suitably porous to enable fluid to be channeled across the membrane. Moreover, in this embodiment, the membrane is suitably conductive to enable tip assembly 108 to function as described herein.

In one embodiment, tip assembly 108 is particularly suited for ablation procedures, wherein the electrode is energized to deliver radio frequency (RF) waves at a site of an abnormal electrical pathway in the body. RF energy may therefore be applied to biological tissue in proximity to tip assembly 108. Ablation procedures are typically used, for example, within the interior chambers of the heart to thermally ablate cardiac tissue. The electrode may additionally be operated to record intracardiac signals and to provide pacing signals in a unipolar configuration or in a bipolar configuration with a sensing vector to an adjacent electrode coupled to shaft 102 (e.g., a ring-type electrode spaced from tip assembly 108).

Figure 4:
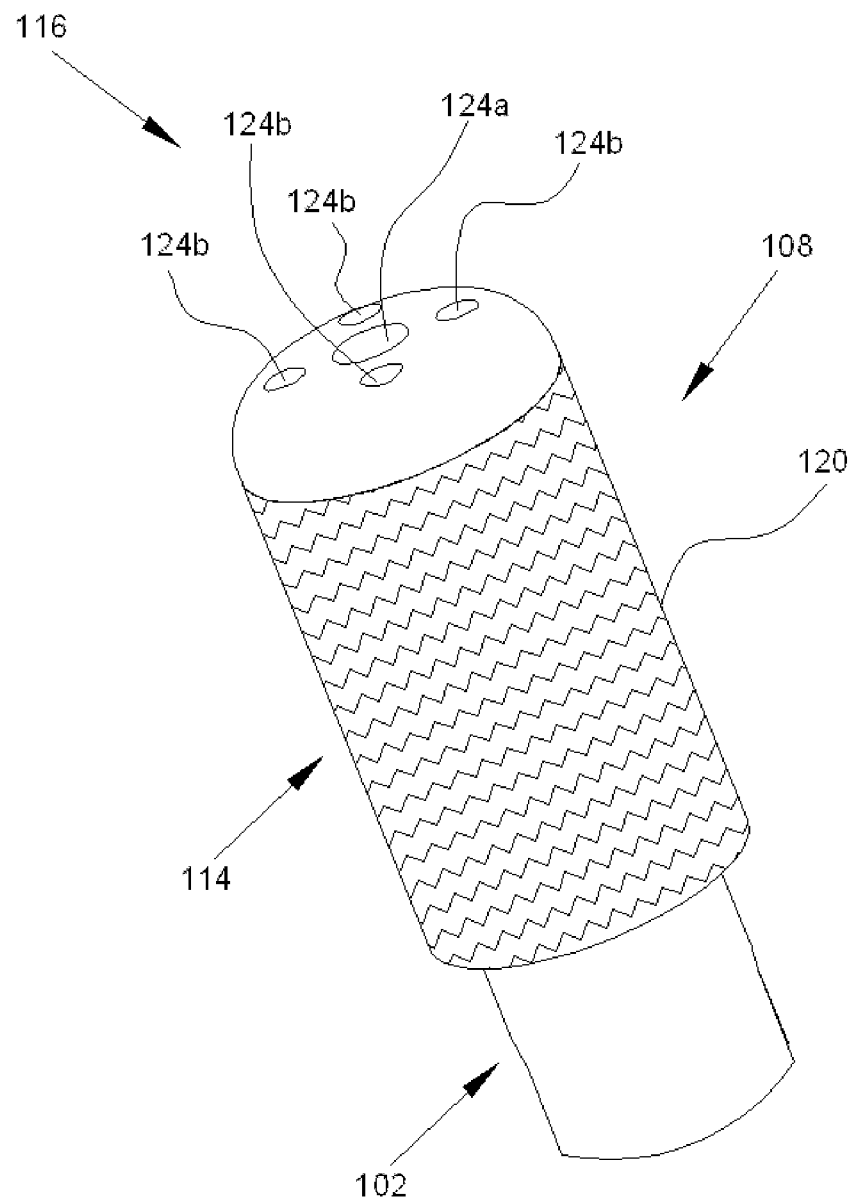
FIG. 4 is a perspective view of another exemplary tip assembly for use with the catheter shown in FIG. 1.

FIG. 4 is a perspective view of an alternate embodiment of tip assembly 108. In the exemplary embodiment, dome tip 116 includes at least one irrigation port or opening 124 extending through sidewall 114 of tip assembly 108. More specifically, in the exemplary embodiment, dome tip 116 includes a central opening 124a and four satellite openings 124b positioned circumferentially about central opening 124a. As shown in FIG. 4, central opening 124a has a first size and each satellite opening 124b has a second size that is smaller than the first size. In the exemplary embodiment, channels 120 have a pattern extending about a circumference of tip assembly 108. In the exemplary embodiment, the pattern is an interlocking dovetail pattern. Alternatively, the pattern can be and, in one embodiment, is any type of interlocking arrangement that provides for relative movement in the proximal and distal direction with regard to either all or part of tip assembly 108. For example, alternative patterns of the interlocking arrangement can be and, in one embodiment, is bulbous, trapezoidal, triangular, rectangular, and any other shape that creates an interlocking fit.

Figure 5:
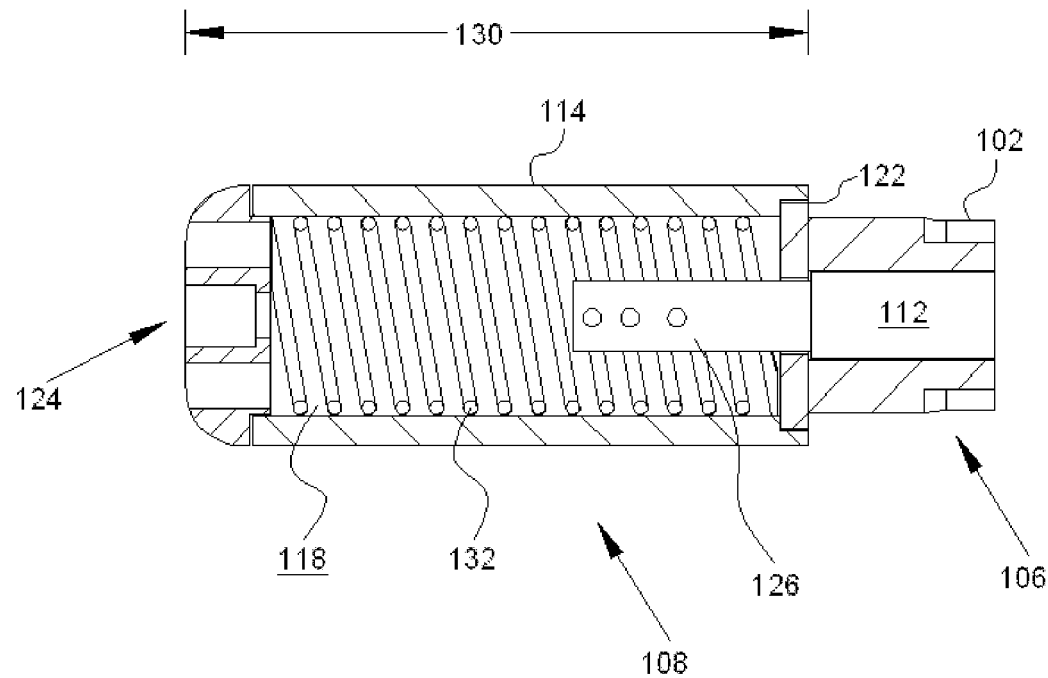

FIG. 5 is a cross-sectional view of tip assembly 108 coupled to distal portion 106 of tubing 102. In the exemplary embodiment, tip assembly 108 is coupled to tubing 102 at an attachment portion 122 via a suitable coupling mechanism such as heat fusion, adhesion, and/or laser welding.

In the exemplary embodiment, catheter 100 is configured to channel an irrigation fluid, such as saline, to an exterior of tip assembly 108. More specifically, in the exemplary embodiment, inner tube 110 is configured to channel fluid to tip assembly 108, wherein the fluid is channeled to opening 124.

As shown in FIG. 5, catheter 100 includes a lumen extension member 126, described in further detail herein below, extending beyond inner tube 110 and into tip assembly 108. In the exemplary embodiment, lumen extension member 126 is coupled to inner tube 110 via a suitable coupling mechanism such as heat fusion, adhesion, and/or laser welding. Alternatively, lumen extension member 126 is formed integrally with inner tube 110.

Lumen extension member 126 defines an extended fluid lumen 128 (shown in FIG. 7) extending therethrough. Lumen extension member 126 enables channeling fluid from inner tube 110 along a longitudinal length 130 of tip assembly 108. As such, extended fluid lumen 128 is in fluid communication with central lumen 112 and/or tip lumen 118 to provide a substantially uniform irrigation pattern or fluid flow within tip assembly 108.

In one embodiment, lumen extension member 126 extends to at least one opening 124 such that lumen extension member 126 is configured to channel a dedicated distribution of fluid to the at least one opening 124. In this embodiment, channeling a dedicated distribution of fluid through lumen extension member 126 facilitates controlling fluid channeled through the at least one opening 124.

Additionally or alternatively, lumen extension member 126 is coupled to a manifold (not shown) that is configured to channel fluid from extended fluid lumen 128 to the at least one opening 124. More specifically, in this embodiment, the manifold couples lumen extension member 126 to the distal end of tip assembly 108 and, more specifically, to distal openings 124. In this embodiment, the manifold is positioned within tip assembly 108 and is fabricated from any suitable material that does not compromise a flexibility of tip assembly 108.

Additionally or alternatively, lumen extension member 126 includes a sidewall (not shown) that defines a second extended fluid lumen (not shown) separate from extended fluid lumen 128. In this embodiment, the sidewall is positioned within lumen extension member 126 such that extended fluid lumen 128 and the second extended fluid lumen are substantially concentric. In this embodiment, the sidewall extends to at least one opening 124 such that the second extended fluid lumen is configured to channel a dedicated distribution of fluid to the at least one opening 124. In this embodiment, channeling a dedicated distribution of fluid through the sidewall facilitates controlling fluid channeled through the at least one opening 124. In this embodiment, the sidewall is fabricated from any suitable material that does not compromise a flexibility of tip assembly 108.

In the exemplary embodiment, tip assembly 108 includes a biasing element, such as a spring coil 132, positioned in tip lumen 118 about lumen extension member 126. Coil 132 provides structural integrity to sidewall 114 and resiliently maintains tip assembly 108 in a predetermined configuration when no force is applied to tip assembly 108. In the exemplary embodiment, the predetermined configuration orients longitudinal length 130 of tip assembly 108 to follow a straight line. Alternatively, the predetermined configuration orients the longitudinal length of tip assembly 108 along a curved or arcuate path.

In the exemplary embodiment, coil 132 resiliently biases tip assembly 108 to axially stretch in the longitudinal direction. When deflected from the predetermined configuration under applied force, tip assembly 108 resiliently returns to the predetermined configuration when the applied force is released.

In the exemplary embodiment, tip assembly 108 and/or coil 132 are, in one embodiment, fabricated from a shape memory material that facilitates positioning tip assembly 108 and/or coil 132 in the predetermined configuration. In one embodiment, tip assembly 108 is fabricated from a compliant material that has balloon-like properties including being configured to expand, deflate, and/or adjust when a fluid is channeled therethrough. In another embodiment, tip assembly 108 is fabricated from a noncompliant material that is configured to maintain a rigid overall shape when a fluid is channeled therethrough while optionally still allowing flexibility and directionality of irrigation fluid toward a contacted surface.

In the exemplary embodiment, tip assembly 108 can be and, in one embodiment, is made of biocompatible materials that are suitable for ablation temperatures. Such materials include, without limitation, natural and synthetic polymers, various metals and metal alloys, Nitinol, naturally occurring materials, textile fibers, and combinations thereof. In the exemplary embodiment, tip assembly 108, and other catheter components including, without limitation, lumen extension member 126 and coil 132, are fabricated from a non-magnetic, non-electrically conductive, and non-RF reactive material to enable magnetic resonance imaging (MRI) of tip assembly 108 using an MRI system (not shown) for positioning and/or orienting tip assembly 108. While catheter 100 is advantageous for use with an MRI system, it is contemplated that magnetic fields and gradients to generate images of tip assembly 108 may alternatively be generated by other systems and techniques if desired. For example, in one embodiment, tip assembly 108 is fabricated from 90% platinum and 10% iridium, or other materials known in the art, such that tip assembly 108 is viewable under fluoroscopic exposure.

Alternatively, tip assembly 108 is fabricated from a conductive material to enable navigating tip assembly 108 to a site in the body where a medical procedure, such as atrial mapping, pacing and/or ablation, is to occur. In the alternative embodiment, a magnetic field is applied when distal portion 106 is extended into a heart chamber of a patient to cause the conductive material in tip assembly 108 to respond to the applied magnetic field for precisely positioning tip assembly 108 at a specific location. In the alternative embodiment, the magnetic fields used to orient tip assembly 108 are generated with a magnetic stereotactic system (not shown). Such stereotactic systems are known and are commercially available from, for example, Stereotaxis of St. Louis, Mo. While catheter 100 is advantageous for use with a stereotactic system, it is contemplated that magnetic fields and gradients to deflect tip assembly 108 may alternatively be generated by other systems and techniques if desired. Additionally or alternatively, tip assembly 108 may include and/or be coated with a conductive material including, without limitation, gold and/or platinum, to increase a thermal conductivity of the electrodes. Moreover, tip assembly 108 can be and, in one embodiment, is coated with heparin to provide an anticoagulation effect. Furthermore, tip assembly 108 can be and, in one embodiment, is electro-polished to reduce sharp edges.

Figure 6:
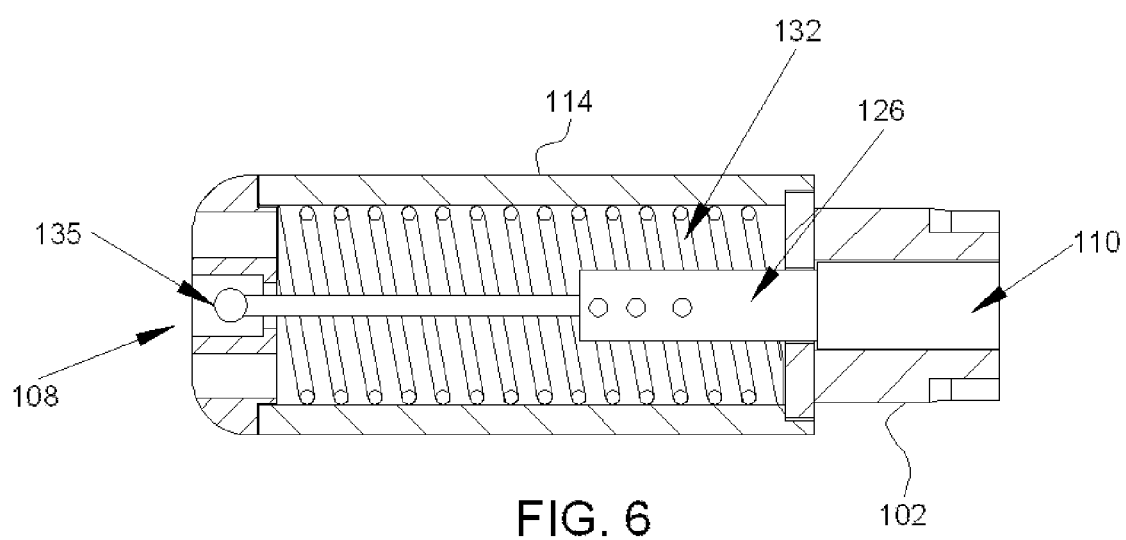

FIG. 6 is a cross-sectional view of the embodiment of tip assembly 108 shown in FIG. 4. In the exemplary embodiment, tip assembly 108 has flexible properties and is configured to bend in a suitable direction. In the exemplary embodiment, tip assembly 108 is configured to bend approximately 20° from a longitudinal axis of tip assembly 108.

In the exemplary embodiment, tip assembly 108 includes a temperature sensor 135 to facilitate monitoring an operating temperature of tip assembly 108. More specifically, in the exemplary embodiment, temperature sensor 135 is a thermocouple-type temperature sensor positioned proximate dome tip 116 to ensure that overheating does not occur in tip assembly 108 and/or the tissues that surround tip assembly 108.

Figure 7:
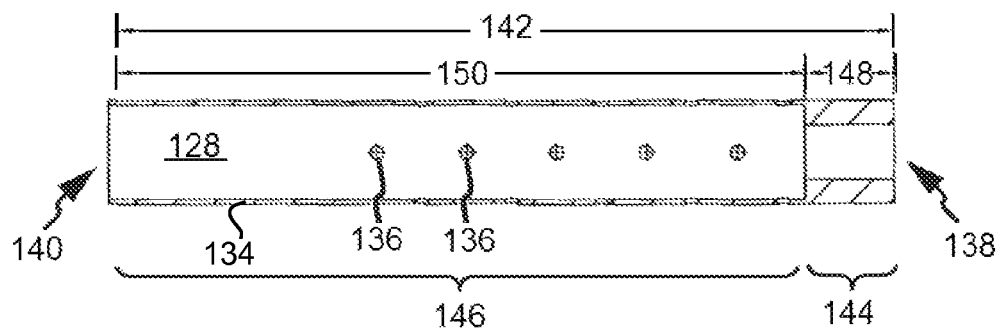
FIG. 7 is a cross-sectional view of an exemplary lumen extension member for use with the tip assembly shown in FIG. 3.
Figure 8:
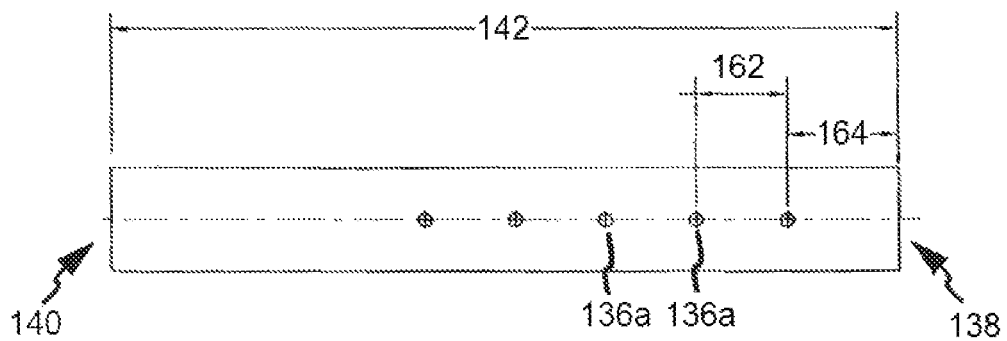
FIG. 8 is a side view of the lumen extension member shown in FIG. 7.
Figure 9:
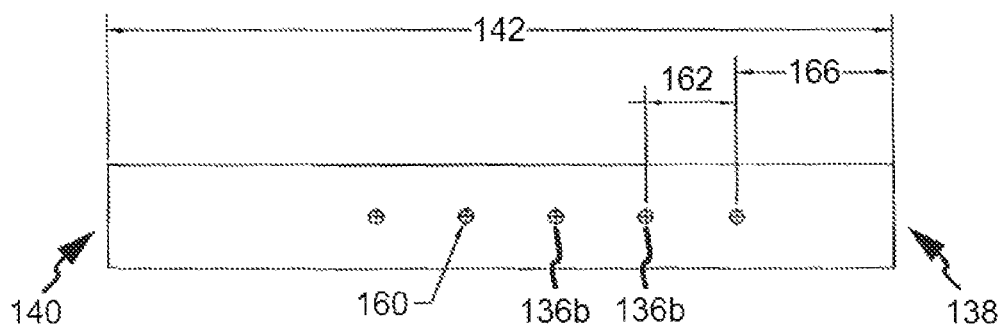
Figures 10, 11:
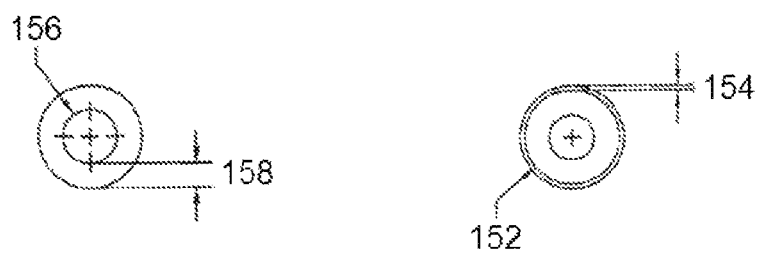
FIG. 10 is a proximal end view of the lumen extension member shown in FIG. 7.
FIG. 11 is a distal end view of the lumen extension member shown in FIG. 7.

FIG. 7 is a cross-sectional view of lumen extension member 126, and FIGS. 6-9 provide orthogonal views of lumen extension member 126. In the exemplary embodiment, lumen extension member 126 includes a sidewall 134 having a plurality of openings 136 extending therethrough. Openings 136, described in further detail herein below, have diameters, shapes, numbers, and/or distributions that may vary from design to design and from a proximal end 138 to a distal end 140, depending upon the application.

Inner tube 110 and/or lumen extension member 126 can be and, in one embodiment, is fabricated from a suitable biocompatible material including at least one of a polyimide material, a polyether block amide material, a silicone material, and a polyurethane material. In the exemplary embodiment, lumen extension member 126 is fabricated from a material that is substantially similar to the material used to fabricate inner tube 110. Alternatively, lumen extension member 126 can be and, in one embodiment, is fabricated from a biocompatible material that is different from the biocompatible material used to fabricate inner tube 110. In the exemplary embodiment, lumen extension member 126 is fabricated from a polyimide material.

Lumen extension member 126 may have any suitable cross-sectional shape to enable channeling fluid therethrough. In the exemplary embodiment, lumen extension member 126 has a substantially rounded cross-sectional shape such as one of a circle, an ellipse, and an oval. Moreover, lumen extension member 126 may have any suitable number of portions each having any suitable geometry extending along a longitudinal length 142 of lumen extension member 126. For example, lumen extension member 126 may have a substantially uniform geometry extending along longitudinal length 142 of lumen extension member 126. Moreover, lumen extension member 126 may have a funnel-shaped geometry extending along longitudinal length 142 of lumen extension member 126. For example, a funnel-shaped lumen-extension member 126 has a diameter that gradually increases along longitudinal length 142 of lumen extension member 126 from proximal end 138 to distal end 140. In the exemplary embodiment, lumen extension member 126 includes a proximal portion 144 having a first geometry and a distal portion 146 having a second geometry.

Lumen extension member 126 may have any suitable length that does not compromise a flexibility of tip assembly 108. Lumen extension member 126 can be formed of, or is partially or entirely coated or lined with, a thermally conductive material to insulate the irrigation fluid, chemicals, therapeutic substances, gels, cooling or heating solutions, and the like from the body or electrode energy. In the exemplary embodiment, lumen extension member 126 has a length that is up to approximately 90 percent of a length of tip assembly 108. For example, in the exemplary embodiment, tip assembly 108 has a longitudinal length 130 of approximately 2.0 mm to approximately 8.0 mm, and lumen extension member 126 has a longitudinal length 142 of approximately 1.8 mm to approximately 7.2 mm. More specifically, in the exemplary embodiment, proximal portion 144 has a longitudinal length 148 of approximately 0.13 mm to approximately 0.55 mm, and distal portion 146 has a longitudinal length 150 of approximately 1.67 mm to approximately 6.65 mm.

Sidewall 134 may have any suitable configuration. In the exemplary embodiment, sidewall 134 has a configuration that is different from a configuration of inner tube 110. Moreover, in the exemplary embodiment, a sidewall of proximal portion 144 has a configuration that is different from a configuration of a sidewall of distal portion 146.

In the exemplary embodiment, openings 136 extend through sidewall 134 to enable channeling fluid flow along longitudinal length 130 of tip assembly 108. Each opening 136 may have any suitable configuration. In the exemplary embodiment, each opening 136 has a substantially rounded shape such as a circle, an ellipse, and an oval. Moreover, in the exemplary embodiment, at least one opening 136 has an axis that is substantially perpendicular to longitudinal length 142 of lumen extension member 126. Furthermore, in the exemplary embodiment, at least one opening 136 has a diameter 160 of approximately 0.05 mm to approximately 0.20 mm. In the embodiment shown in FIG. 6, openings 136 include a first opening proximate proximal end 138 of lumen extension member 126 having a first diameter, and a second opening proximate distal end 140 of lumen extension member 126 having a second diameter that is smaller than the first diameter.

In the exemplary embodiment, the plurality of openings 136 include a first plurality of openings 136*a* and a second plurality of openings 136*b*. First and second pluralities of openings 136*a* and 136*b* each may include any suitable quantity of openings. For example, first plurality of openings 136*a* may include a first quantity of openings, and second plurality of openings 136*b* may include a second quantity of openings. In the exemplary embodiment, the first quantity is equal to the second quantity. Alternatively, the first quantity can be and, in one embodiment, is different from the second quantity.

In the exemplary embodiment, first and second pluralities of openings 136*a* and 136*b* each are positioned along longitudinal length 142 of lumen extension member 126. In the exemplary embodiment, first and second pluralities of openings 136*a* and 136*b* each include openings 136 that are positioned a distance 162 of approximately 0.51 mm apart in the longitudinal direction. Moreover, in the exemplary embodiment, first plurality of openings 136*a* is spaced longitudinally apart from second plurality of openings 136*b*.

In the exemplary embodiment, first plurality of openings 136*a* is spaced radially apart from second plurality of openings 136*b*. More specifically, in the exemplary embodiment, first plurality of openings 136*a* is positioned approximately 90 degrees from second plurality of openings 136*b*. In the exemplary embodiment, first plurality of openings 136*a* includes a first pair of diametrically opposed openings, and second plurality of openings 136*b* includes a second pair of diametrically opposed openings. More specifically, in the exemplary embodiment, first plurality of openings 136*a* is positioned on a first plane and second plurality of openings 136*b* is positioned on a second plane that is substantially perpendicular to the first plane.

The many embodiments of ablation catheters facilitate the following exemplary methods of providing a radially directed irrigation flow pattern that is substantially uniform along a longitudinal length of a tip assembly coupled to the catheter. A fluid is channeled through inner tube 110 to lumen extension member 126. The fluid is then channeled through extended lumen 128 to facilitate channeling fluid flow along the longitudinal length of tip assembly 108. More specifically, the fluid is channeled through at least one opening 136 positioned along the longitudinal length of lumen extension member 126. The configuration of openings 136 facilitates providing a radially directed irrigation flow pattern that is substantially uniform along a longitudinal length of tip assembly 108, when the tip assembly 108 is in an unflexed position. When the tip assembly 108 is in a flexed position such as when it impinges upon a surface at an angle, the flow of the irrigating fluid varies along the longitudinal length of tip assembly 108 due to the variations in opening size of channels 120. More fluid flows toward the surface than away from the surface due to the channels 120 becoming more open toward the surface and less open away from the surface.

Thus, specific embodiments and applications of flexible tip electrodes have been described. It should be apparent, however, to those skilled in the art that many more modifications besides those already described are possible without departing from the inventive concepts herein. The inventive subject matter, therefore, is not to be restricted except in the spirit of the appended claims.

Although a number of embodiments of this invention have been described above with a certain degree of particularity, those skilled in the art could make numerous alterations to the disclosed embodiments without departing from the spirit or scope of this invention. For example, all joinder references (e.g., attached, coupled, connected, and the like) are to be construed broadly and may include intermediate members between a connection of elements and relative movement between elements. As such, joinder references do not necessarily infer that two elements are directly connected and in fixed relation to each other. It is intended that all matter contained in the above description or shown in the accompanying drawings shall be interpreted as illustrative only and not limiting. Changes in detail or structure may be made without departing from the spirit of the invention as defined in the appended claims.

What is claimed is:

1. A catheter comprising:
    a catheter body comprising a distal portion;
    an electrode configured to be biased to an expanded configuration and to allow shortening when a force is applied to the electrode;
    a lumen extension member fixedly coupled to said catheter body distal portion, said lumen extension member defining a lumen and being flexible; and
    at least one opening extending through said lumen extension member and in fluid communication with said lumen extension member lumen, wherein a distal portion of said lumen extension member is positioned in said electrode and is spaced from said electrode when said electrode is in an at rest position.

2. A catheter in accordance with claim 1, wherein a flexibility of said electrode is not compromised by said lumen extension member during initial bending movement of said electrode.

3. A catheter in accordance with claim 1, wherein said electrode comprises a shape memory alloy and is coated with at least one of gold and platinum.

4. A catheter in accordance with claim 1, wherein said electrode comprises a channel extending at least partially therethrough and the channel surrounds at least a portion of said lumen extension member.

5. A catheter in accordance with claim 1, wherein said lumen extension member comprises a proximal portion having a first inner diameter and the distal portion has a second inner diameter that is different from the first inner diameter.

6. A catheter in accordance with claim 1, wherein said lumen extension member has a substantially uniform geometry extending along a longitudinal length thereof.

7. A catheter in accordance with claim 1, wherein said at least one opening comprises a proximal opening having a first configuration and a distal opening having a second configuration that is different from the first configuration.

8. A catheter in accordance with claim 1, wherein said electrode has a first length and is configured to have flexible properties, and said lumen extension member has a second length that is shorter than the first length and is configured such that a flexibility of said electrode is not compromised by said lumen extension member during initial bending movement of said electrode from the at rest position.

9. A catheter in accordance with claim 1, further comprising a biasing element positioned in said electrode about said lumen extension member, said biasing element providing structural integrity to said electrode.

10. A catheter comprising:
a distal portion sized and configured for insertion in a patient;
an electrode connected to said distal portion; and
an irrigation member fixedly connected to said distal portion, wherein said irrigation member extends at least partially within said electrode, is spaced from said electrode, and defines a lumen, and wherein said irrigation member is flexible and said electrode is configured to be biased to an expanded configuration and to allow shortening when a force is applied to said electrode.

11. A catheter in accordance with claim 10, wherein said irrigation member comprises a proximal portion having a first inner diameter and a distal portion having a second inner diameter that is different from the first inner diameter.

12. A catheter in accordance with claim 10, wherein said irrigation member further includes a plurality of openings extending therethrough, said plurality of openings extending along a longitudinal length of said irrigation member.

13. A catheter in accordance with claim 10, wherein said irrigation member has a substantially uniform geometry extending along a longitudinal length thereof.

14. A catheter in accordance with claim 10, wherein said electrode has a first length and is configured to have flexible properties, and said irrigation member has a second length that is shorter than the first length and is configured such that a flexibility of said electrode is not compromised by said irrigation member during initial bending movement of said electrode from an at rest position.

15. A catheter in accordance with claim 10, further comprising a biasing element positioned in said electrode about said irrigation member, said biasing element providing structural integrity to said electrode.

16. A catheter in accordance with claim 10, wherein a flexibility of said electrode is not compromised by said irrigation member during initial bending movement of said electrode.

17. A catheter in accordance with claim 10, wherein said electrode comprises a shape memory alloy and is coated with at least one of gold and platinum.

18. A catheter in accordance with claim 10, wherein said electrode comprises a channel extending at least partially therethrough and the channel surrounds at least a portion of said irrigation member.

19. A catheter in accordance with claim 18, wherein the channel is configured such that fluid from said irrigation member is directed toward an inner portion of said electrode.

* * * * *